United States Patent [19]

Yamaguchi et al.

[11] 4,275,240
[45] Jun. 23, 1981

[54] PROCESS FOR THE PREPARATION OF 2,2'-BISPHENOL SULFOXIDES

[75] Inventors: Akihiro Yamaguchi, Yokohama; Keizaburo Yamaguchi, Kawasaki; Hisamichi Murakami; Tadashi Kobayashi, both of Yokohama, all of Japan

[73] Assignee: Mitsui Toatsu Chemicals, Inc., Tokyo, Japan

[21] Appl. No.: 126,980

[22] Filed: Mar. 3, 1980

[51] Int. Cl.$^3$ ............................................. G07C 147/14
[52] U.S. Cl. ........................................ 568/37; 560/10; 560/11; 562/427; 562/429
[58] Field of Search ...................... 568/37; 560/10, 11; 562/427, 429

[56] References Cited

U.S. PATENT DOCUMENTS

| | | | |
|---|---|---|---|
| 2,661,376 | 12/1953 | Comer et al. | 568/37 |
| 4,089,904 | 5/1978 | Cisney et al. | 568/37 |
| 4,108,866 | 8/1978 | Tramier et al. | 568/37 |

OTHER PUBLICATIONS

J. Drabowicz et al., Chem. Abstracts, 90:22488a (1979), A Facile & Selective Oxidation of Organic Sulfides to Sulfoxides with $H_2O_2/SeO_2$.
V. Laba et al., Chem. Abstracts, 86:120980s (1977), Sulfoxides.
W. Gump et al., JACS, 67, 238 (1945).
L. Nikolenko et al., J. Gen'l. Chem. USSR, 33, 3664 (1963).
Drabowicz et al., A Facile and Selective Oxidation of Organic Sulphides to Sulphoxides with Hydrogen Peroxide/Selenium Dioxide System, *Synthesis*, pp. 758-759, (Oct. 1978).

*Primary Examiner*—Donald G. Daus
*Assistant Examiner*—M. C. Eakin
*Attorney, Agent, or Firm*—Fisher, Christen & Sabol

[57] ABSTRACT

2,2'-Bisphenol sulfoxides are prepared by oxidizing 2,2'-bisphenol sulfides with hydrogen peroxide in the presence of such an organic solvent as not to form any organic peracids under reaction conditions.

9 Claims, No Drawings

PROCESS FOR THE PREPARATION OF 2,2'-BISPHENOL SULFOXIDES

BACKGROUND OF THE INVENTION

This invention relates to a novel process for the preparation of 2,2'-bisphenol sulfoxides.

Generally, it is almost impossible to confine the oxidation reaction of aromatic sulfides solely to the formation of sulfoxides, and the problem is in that sulfones as by-products are incorporated in the reaction mixture. It has been recommended to use exclusively a particular oxidizing agent such as N-bromosuccinimides, bromine complexes of diazabicyclo[2,2,2]-octane, pyridine or quinolines, and the like in order to prepare solely sulfoxides at such a high selectivity that no sulfone is produced due to a side reaction.

Glacial acetic acid (peracetic acid oxidation) has been predominantly used as a solvent in the oxidation reaction of aromatic sulfides with hydrogen peroxide. However, it is difficult to prepare solely sulfoxides with selectively even with a theoretical amount of hydrogen peroxide used, because the sulfoxide itself is readily oxidized to form a sulfone.

That is, in many cases, the oxidation process of aromatic sulfides with hydrogen peroxide is essentially employed for the purpose of the preparation of the corresponding sulfones. The oxidation of known 2,2'-bisphenol sulfides with hydrogen peroxide is also effected in the presence of glacial acetic acid to obtain the corresponding 2,2'-bisphenol sulfones (J. Am. Chem. Soc., 67, 238 (1945)).

SUMMARY OF THE INVENTION

An object of the present invention is to provide a process for the preparation of 2,2'-bisphenol sulfoxides, in which 2,2'-bisphenol sulfides are oxidized to obtain the corresponding 2,2'-bisphenol sulfoxides at a high yield with a little or no by-product formed.

From such a standpoint that hydrogen peroxide is advantageous as oxidizing agent in that it is inexpensive and can be handled easily, and that the post treatment after reaction is made easier, and so forth, an extensive study was made on the oxidation reaction of 2,2'-bisphenol sulfides with hydrogen peroxide. As a result, it was found that 2,2'-bisphenol sulfides can be oxidized to obtain the corresponding 2,2'-bisphenol sulfoxides by effecting the oxidation reaction with hydrogen peroxide in the presence of a conventional organic solvent excluding an organic acid such as glacial acetic acid, formic acid, and the like, which forms an organic peracid with hydrogen peroxide.

That is, the process of the present invention relates to a process for the preparation of 2,2'-bisphenol sulfoxides, preferably 2,2'-bisphenol sulfoxides represented by the general formula (I)

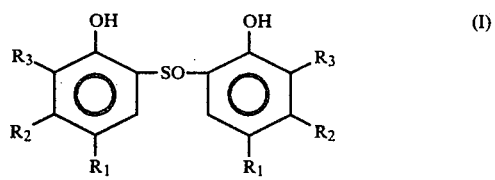
(I)

where $R_1$, $R_2$, and $R_3$ are selected from hydrogen atom, a halogen atom, an alkyl radical, a cycloalkyl radical, an aryl radical, an aralkyl radical, hydroxyl group, an alkoxy radical, an allyloxy radical, carboxyl group, and a carboalkoxy radical, or $R_1$ and $R_2$, $R_2$ and $R_3$ or $R_1$, $R_2$ and $R_3$ may form a ring together with the carbons of the benzene nucleus to which these radicals bond respectively, by oxidizing 2,2'-bisphenol sulfides, preferably 2,2'-bisphenol sulfides represented by the general formula (II)

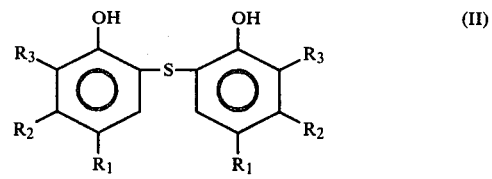
(II)

where $R_1$, $R_2$, and $R_3$ have the same meanings as defined above for the general formula (I), with hydrogen peroxide in the presence of such an organic solvent as not to form any organic peracids under reaction conditions.

In accordance with the present invention, the oxidation reaction proceeds desirably with a theoretical amount of hydrogen peroxide used, but even with a large excess of hydrogen peroxide used, no sulfones are formed, and moreover formation of other by-products due to oxidation was not recognized to obtain the corresponding bisphenol sulfoxides of an extremely high purity at an approximately quantitative yield with great industrial advantages.

DETAILED DESCRIPTION OF THE INVENTION 2,2'-bisphenol sulfides used in the process of the present invention are preferably any compounds represented by the general formula (II)

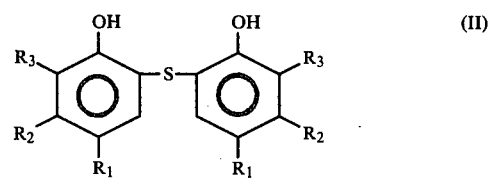
(II)

where $R_1$, $R_2$, and $R_3$ are selected from hydrogen atom, a halogen atom, an alkyl radical, a cycloalkyl radical, an aryl radical, an aralkyl radical, hydroxyl group, an alkoxy radical, an allyloxy radical, carboxyl group, and a carboalkoxy radical, or $R_1$ and $R_2$, $R_2$ and $R_3$ or $R_1$, $R_2$ and $R_3$ may form a ring together with carbons of the benzene nucleus to which these radicals bond respectively.

Examples of the above-mentioned compounds include
2,2'-diphenol sulfide,
2,2'-bis(4-methylphenol)sulfide,
2,2'-bis(6-methylphenol)sulfide,
2,2'-bis(4-iso-propylphenol)sulfide,
2,2'-bis(4-n-butylphenol)sulfide,
2,2'-bis(4-sec-butylphenol)sulfide,
2,2'-bis(4-tert-butylphenol)sulfide,
2,2'-bis(6-tert-butylphenol)sulfide,
2,2'-bis(4-tert-amylphenol)sulfide,
2,2'-bis(4-tert-octylphenol)sulfide,
2,2'-bis(4-nonylphenol)sulfide,
2,2'-bis(4-tert-butyl-6-methylphenol)sulfide,
2,2'-bis(4-methyl-6-tert-butylphenol)sulfide, 2,2'-bis(4,6-dimethylphenol)sulfide,
2,2'-bis(4,6-di-tert-butylphenol)sulfide,
2,2'-bis(4,5-dimethylphenol)sulfide,
2,2'-bis(4-cyclohexylphenol)sulfide,
2,2'-bis(4-cyclohexyl-6-methylphenol)sulfide,
2,2'-bis(4,6-dicyclohexylphenol)sulfide,
2,2'-bis(4-α,α'-dimethylbenzylphenol)sulfide,
2,2'-bis(4-benzylphenol)sulfide,
2,2'-bis(4,6-dibenzylphenol)sulfide,
2,2'-bis(4-phenylphenol)sulfide,
2,2'-bis(4-phenyl-6-methylphenol)sulfide,
2,2'-bis(4-α,α'-dimethylbenzyl-6-phenylphenol)sulfide,
2,2'-bis(4-chlorophenol)sulfide,
2,2'-bis(4,6-dichlorophenol)sulfide,
2,2'-bis(4,5,6-trichlorophenol)sulfide,
2,2'-bis(4-bromophenol)sulfide,
2,2'-bis(4,6-dibromophenol)sulfide,
2,2'-bis(4-hydroxyphenol)sulfide,
2,2'-bis(4,6-dimethoxyphenol)sulfide,
2,2'-bis(4-carboxyphenol)sulfide,
2,2'-bis(4-carbomethoxyphenol)sulfide,
2,2'-bis(4-carbobutoxyphenol)sulfide,
1,1'-bis(2-naphthol)sulfide,
2,2'-bis(1-naphthol)sulfide and the like.

The organic solvent used in the process of the present invention includes any conventional organic solvents excluding any organic acids which form organic peracids with hydrogen peroxide, and more specifically includes hydrocarbons such as hexane, cyclohexane, heptane, benzene, toluene, xylene and ethylbenzene; halogenated hydrocarbons such as dichloromethane, chloroform, carbon tetrachloride, dichloroethane, trichloroethane, chlorobenzene and o-dichlorobenzene; alcohols such as methanol, ethanol, propanol and butanol; ethers such as diethyl ether, dibutyl ether, tetrahydrofuran and dioxane; ketones such as acetone and methylethylketone; esters such as acetic acid esters and propionic acid esters; aprotic polar solvents such as N,N-dimethylformamide, dimethylsulfoxide, and N-methyl pyrrolidone, carbon disulfide, and the like.

The above solvents may be used as a mixture thereof, or as a mixture thereof with water.

The use of hydrocarbon and halogenated hydrocarbon solvents immiscible with water specifically such as benzene, toluene, xylene, chlorobenzene, dichloroethane and carbon tetrachloride among those solvents to be recovered by steam distillation after completion of the reaction. The thus recovered solvents can be directly reused by circulation, and if required, can be further subjected to a purification treatment such as distillation for reuse, which results in not only serving the reduction of solvents used leading to reducing the cost, but also decreasing the problems associated with environmental protections with great industrial advantages.

The solvent is generally used in an amount of from 0.5 to 10 parts by volume and preferably from about 2 to 5 parts by volume per one part by weight of the sulfide as starting material.

Hydrogen peroxide is used as an aqueous hydrogen peroxide at various concentrations, and preferably as an aqueous hydrogen peroxide at a concentration in the range of from 30 to 35% due to an easiness in its handling. Hydrogen peroxide is usually used in a little excess over the amount theoretically required, but can also be used in an amount in the range of from 1.5 to 5.0 times the amount theoretically required. Hydrogen peroxide is subjected to the oxidation reaction either by adding it drop by drop to a solution of the sulfide and the solvent used, or by mixing it with the solution in advance.

The reaction of the present invention is usually carried out at a temperature of from 30° to 110° C. If the reaction temperature is lower than 30° C., the reaction requires a long period of time, while if the reaction temperature is higher than 110° C., the concentration of hydrogen peroxide is extremely reduced, and unfavorable phenomena such as bubbling take place, which results in preventing the reaction from taking place. The reaction temperature is more preferably of from 50° to 100° C.

In the practice of the process of the present invention, generally 2,2'-bisphenol sulfide is dissolved in a solvent mentioned above. While this solution is kept at a temperature of 30°–110° C., an aqueous hydrogen peroxide is added thereto drop by drop. After the addition by dropping of the aqueous hydrogen peroxide is completed, the resulting reaction mixture is stirred at that temperature for additional 30 minutes to 5 hours, and then either is allowed to cool to room temperature followed by diluting it with water, or is subjected to steam distillation to distill off the solvent followed by allowing the residual solution to cool to room temperature to form a precipitate. The precipitate is separated by filtration, washed with water, and dried to obtain the final product.

In both cases mentioned above, 2,2'-bisphenol sulfoxides can be obtained at a high yield of 95% or above as a product of such a high purity as to be directly used without being subjected to additional procedures specifically as light stabilizers, polyolefin modifiers, lubricant additives, agricultural chemicals, or intermediates thereof.

2,2'-bisphenol sulfides used in the present invention can be prepared by known processes, for example, by reacting a substituted phenol with sulfur dichloride.

To further illustrate this invention, and not by way of limitation, the following examples are given.

EXAMPLE 1

In 30 ml of ethanol was dissolved 6.6 g (0.02 mole) of 2,2'-bis(4-tert-butylphenol)sulfide. While this solution was kept at a temperature of 70°–75° C., 3.4 g (0.03 mole) of 30% aqueous hydrogen peroxide was added thereto drop by drop over a period of 20 minutes. The resulting reaction mixture was stirred at that temperature for an additional hour, and then was allowed to cool to room temperature followed by adding thereto 100 ml of water to form a precipitate. The precipitate so formed was separated by filtration, washed with water, and dried to obtain a yield of 6.8 g (98.5% of theory) of 2,2'-bis(4-tert-butylphenol)sulfoxide having a melting point in the range of from 150° to 152° C. Then, the above product was further subjected to recrystallization from n-hexane to obtain a pure product melting at a temperature of 152°–153° C. as white needle-like crystals.

The results of elemental analysis were as follows:

|  | C(%) | H(%) | S(%) |
|---|---|---|---|
| Calculated Values | 69.3 | 7.56 | 9.30 |
| Found Values | 69.6 | 7.76 | 9.07 |

EXAMPLES 2-6

The procedure of Example 1 was repeated except that 2,2'-bisphenol sulfides were used to obtain the corresponding 2,2'-bisphenol sulfoxide compounds as shown in Table-1.

TABLE 1

| Example | 2,2'-bisphenol sulfoxide | Yield (%) | Melting Point (°C.) | Values by Elemental Analysis | | |
|---|---|---|---|---|---|---|
| | | | | C | H | S*(%) |
| No. 2 | 2,2'diphenol sulfoxide | theoretical | 172–173 | 61.7 (61.5) | 4.18 (4.30) | 13.4 (13.7) |
| No. 3 | 2,2'-bis(4-cyclohexylphenol)-sulfoxide | 98.0 | 218–219 | 72.8 (72.3) | 7.38 (7.59) | 8.15 (8.04) |
| No. 4 | 2,2'-bis(4-α,α'-dimethylbenzylphenol)sulfoxide | 97.5 | 147–148 | 76.6 (76.7) | 6.43 (6.49) | 6.81 (6.61) |
| No. 5 | 2,2'-bis(4-phenylphenol) sulfoxide | 95.0 | 202–204 | 74.9 (74.6) | 4.62 (4.69) | 8.41 (8.30) |
| No. 6 | 1,1'-bis(2-naphthol) sulfoxide | 96.0 | 162° C. (decomposed) | 71.2 (71.8) | 4.23 (4.22) | 9.63 (9.59) |

*Values in brackets shown calculated values.

EXAMPLE 7

In a mixture of 20 ml of dioxane and 20 ml of water was dissolved 14.4 g (0.05 mole) of 2,2'-bis(4-chlorophenol)sulfide. While this solution was kept at a temperature of 60°–65° C., 8.0 g (0.07 mole) of 30% aqueous hydrogen peroxide was added thereto drop by drop over a period of 20 minutes. The resulting reaction mixture was stirred at that temperature for additional two hours, and then was allowed to cool to room temperature followed by adding thereto 150 ml of water to form a precipitate. The precipitate so formed was separated by filtration, washed with water, and dried to obtain a yield of 14.4 g (95% of theory) of 2,2'-bis(4-chlorophenol)sulfoxide having a melting point of from 203° to 204° C. Then, the above product was further subjected to recrystallization from an aqueous ethanol to obtain a pure product melting at a temperature of 204°–205° C. as white needle-like crystals.

The results of elemental analysis were as follows:

| | C(%) | H(%) | Cl(%) | S(%) |
|---|---|---|---|---|
| Calculated Values | 47.5 | 2.66 | 10.6 | 23.4 |
| Found Values | 47.7 | 2.78 | 10.3 | 23.2 |

EXAMPLE 8

In 40 ml of carbon tetrachloride was dissolved 12.3 g (0.05 mole) of 2,2'-bis(4-methylphenol)sulfide. While this solution was kept at a temperature of 70°–76° C., 8.0 g (0.07 mole) of 30% aqueous hydrogen peroxide was added thereto drop by drop over a period of 20 minutes. The resulting reaction mixture was stirred at that temperature for additional two hours, and then was subjected to steam distillation to distill off carbon tetrachloride, forming a precipitate. The precipitate thus formed was separated by filtration, and dried to obtain a yield of 12.6 g (96.5% of theory) of 2,2'-bis(4-methylphenol)sulfoxide having a melting point of from 190°–191° C. Then the above product was further subjected to recrystallization from glacial acetic acid to obtain a pure product melting at a temperature of 191°–192° C. as white prism-like crystals.

The results of elemental analysis were as follows:

| | C(%) | H(%) | S(%) |
|---|---|---|---|
| Calculated Values | 64.1 | 5.37 | 12.2 |
| Found Values | 64.6 | 5.40 | 12.4 |

EXAMPLE 9

The procedure of Example 8 was repeated except that 2,2'-bis(4,6-dichlorophenol)sulfide was used instead of 2,2'-bis(4-methylphenol)sulfide to obtain 2,2'-bis(4,6-dichlorophenol)sulfoxide melting at 219°–220° C. at a yield of 97.5% of theory. The above product was further subjected to recrystallization from ethanol to obtain a pure product melting at 223°–224° C. as white needle-like crystals. The results of elemental analysis were as follows:

| | C(%) | H(%) | Cl(%) | S(%) |
|---|---|---|---|---|
| Calculated Values | 38.7 | 1.63 | 38.1 | 8.62 |
| Found Values | 38.5 | 1.70 | 38.3 | 8.68 |

EXAMPLE 10

In 90 ml of benzene was dissolved 44.2 g (0.1 mole) of 2,2'-bis(4-tert-octylphenol)sulfide. While this solution was kept at a temperature of from 75°–80° C., 17 g (0.15 mole) of 30% aqueous hydrogen peroxide was added thereto drop by drop over a period of 30 minutes. The resulting reaction mixture was stirred at that temperature for an additional hour, and then was subjected to steam distillation to distill off benzene, forming a precipitate. The precipitate so formed was separated by filtration and dried to obtain a yield of 45.1 g (98.5% of theory) of 2,2'-bis(4-tert-octylphenol)sulfoxide melting at 169°–170° C. The above product was further subjected to recrystallization from ethanol to obtain a pure product melting at 171°–172° C. as white needle-like crystals. The results of elemental anaylsis were as follows:

| | C(%) | H(%) | S(%) |
|---|---|---|---|
| Calculated Values | 73.3 | 9.24 | 6.99 |

|  | C(%) | H(%) | S(%) |
|---|---|---|---|
| Found Values | 73.8 | 9.35 | 6.83 |

EXAMPLE 11

In 60 ml of benzene was dissolved 44.2 g (0.1 mole) of 2,2'-bis(4-tert-octylphenol)sulfide, and 40 ml of water was added thereto. While this solution was kept at a temperature of from 35° to 40° C., 17 g (0.15 mole) of 30% aqueous hydrogen peroxide was added thereto drop by drop over a period of 30 mintues. The resulting reaction mixture was stirred at that temperature for additional four hours, and then was subjected to steam distillation to distill off benzene, forming a precipitate. The precipitate so formed was separated by filtration, and dried to obtain 2,2'-bis(4-tert-actylphenol)sulfoxide melting at 169°–171° C. at a yield of 98% of theory.

EXAMPLE 12

The procedure of Example 10 was repeated except that 2,2'-bis(4-bromophenol)sulfide was used instead of 2,2'-bis(4-tert-octylphenol)sulfide to obtain 2,2'-bis(4-bromophenol)sulfoxide melting at 201°–203° C. at a yield of 96% of theory. The above product was further subjected to recrystallization from ethanol to obtain a pure product melting at 204°–205° C. as white needle-like crystals.

The results of elemental analysis were as follows:

|  | C(%) | H(%) | Br(%) | S(%) |
|---|---|---|---|---|
| Calculated Values | 36.8 | 2.06 | 40.7 | 8.17 |
| Found Values | 37.0 | 2.03 | 40.8 | 8.21 |

EXAMPLE 13

The procedure of Example 10 was repeated except that 2,2'-bis(4-methyl-6-tert-butylphenol)sulfide was used instead of 2,2'-bis(p-tert-octylphenol)sulfide to obtain 2,2'-bis(4-methyl-6-tert-butylphenol)sulfoxide melting at 120°–121° C. at a yield of 97.5% of theory. The above product was further subjected to recrystallization from ethanol to obtain a pure product melting at 122°–123° C. as white needle-like crystals.

The results of elemental analysis were as follows:

|  | C(%) | H(%) | S(%) |
|---|---|---|---|
| Calculated Values | 70.5 | 8.07 | 8.56 |
| Found Values | 70.4 | 8.26 | 8.42 |

EXAMPLE 14

The procedure of Example 10 was repeated except that 35.8 g (0.1 mole) of 2,2'-bis(4-tert-amylphenol)sulfide was dissolved in 70 ml of o-dichlorobenzene to obtain 2,2'-bis(4-tert-amylphenol)sulfoxide melting at 120°–121° C. at a yield of 96.5% of theory. The above product was further subjected to recrystallization to obtain a pure product melting at 122°–124° C. as white needle-like crystals.

The results of elemental analysis were as follows: A

|  | C(%) | H(%) | S(%) |
|---|---|---|---|
| Calculated Values | 70.5 | 8.07 | 8.56 |
| Found Values | 70.6 | 8.26 | 8.54 |

What is claimed is:

1. A process for the preparation of 2,2'-bisphenol sulfoxides represented by the formula

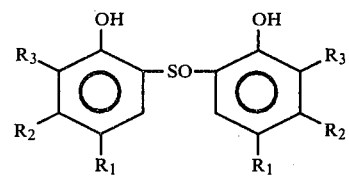

where $R_1$, $R_2$ and $R_3$ are selected from a hydrogen atom, a halogen atom, an alkyl group having 1 to 9 carbon atoms, a cycloalkyl group, a phenyl group, a hydroxy group, an aralkyl group having 7 to 9 carbon atoms, an alkoxy group, an allyloxy group, a carboxyl group and a carboalkoxy group having 2 to 5 carbon atoms or $R_1$ and $R_2$ or $R_2$ and $R_3$ may form a benzene ring together with the bonding carbon atoms respectively, consisting essentially of oxidizing 2,2'-bisphenol sulfides represented by the formula

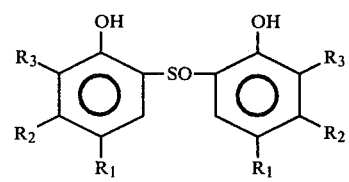

where $R_1$, $R_2$, and $R_3$ have the same meaning as defined above, with hydrogen peroxide in the presence of an organic solvent which does not form an organic peracid with hydrogen peroxide, said organic solvent being selected from aliphatic, alicyclic, and aromatic hydrocarbons, alcohols, ethers, ketones, esters, aprotic polar solvents, carbon disulfide, and mixtures thereof, thereby forming said 2,2'-bisphenol sulfoxides.

2. A process as claimed in claim 1 wherein said organic solvent is selected from hexane, cyclohexane, heptane, benzene, toluene, xylene, ethylbenzene, dichloromethane, chloroform, carbon tetrachloride, dichloroethane, trichloroethane, chlorobenzene, o-dichlorobenzene, methanol, ethanol, propanol, butanol, diethyl ether, dibutyl ether, tetrahydrofuran, dioxane, acetone, methylethylketone, acetic acid esters, propionic acid esters, N,N-dimethylformamide, dimethylsulfoxide, N-methyl pyrrolidone, carbon disulfide and mixtures thereof.

3. A process as claimed in claim 2 wherein said organic solvent is selected from hexane, benzene, toluene, xylene, dichloromethane, chloroform, carbon tetrachloride, dichloroethane, chlorobenzene, o-dichlorobenzene, methanol, ethanol, propanol, diethyl ether, tetrahydrofuran, dioxane, acetone and methylethylketone.

4. A process according to claim 1 wherein said organic solvent used is a hydrocarbon or a halogenated hydrocarbon which is immiscible with water, said solvent being recovered by steam distillation after completion of the reaction to obtain said 2,2'-bisphenol sulfoxides as precipitates.

5. A process according to claim 4 or 1 wherein said hydrocarbon and halogenated hydrocarbon solvents are selected from benzene, toluene, xylene, chlorobenzene, dichloroethane and carbon tetrachloride.

6. A process according to claim 1 wherein the amount of said organic solvent is in the range of from 0.5 to 10 parts by volume per one part by weight of 2,2'-bisphenol sulfide as starting material.

7. A process according to claim 1 wherein said hydrogen peroxide is in an amount ranging from an amount theoretically required for the reaction to 5 times the amount theoretically required.

8. A process according to claim 1 wherein the reaction is carried out at a temperature of from 30° to 110° C.

9. A process according to claim 1 wherein said organic solvent used is at least one solvent selected from the group consisting of benzene, toluene, xylene, chlorobenzene, dichloroethane, and carbon tetrachloride, said solvent being recovered by steam distillation after completion of reaction to obtain said 2,2'-bisphenol sulfoxides as precipitates.

* * * * *